United States Patent [19]
Shipp

[11] Patent Number: 5,263,937
[45] Date of Patent: Nov. 23, 1993

[54] TROCAR WITH PROFILE TO REDUCE INSERTION FORCE

[76] Inventor: John I. Shipp, 104 Short Springs Rd., Tullahoma, Tenn. 37388

[21] Appl. No.: 16,922

[22] Filed: Feb. 11, 1993

[51] Int. Cl.$^5$ ............................................. A61M 5/178
[52] U.S. Cl. .................................. 604/164; 604/264; 604/272; 606/167
[58] Field of Search ............................ 128/749–751; 604/22, 23, 26, 27, 93, 158, 164, 166, 170, 171, 264, 272, 273; 606/1, 108, 167, 172, 181, 184, 185

[56] References Cited

U.S. PATENT DOCUMENTS

| | | | |
|---|---|---|---|
| 1,045,906 | 12/1912 | Sweet | 604/164 |
| 3,039,468 | 6/1962 | Price | 604/164 |
| 3,789,852 | 2/1974 | Kim et al. | 604/164 |
| 4,464,169 | 8/1984 | Semm | 604/26 |
| 4,490,136 | 12/1984 | Ekbladh et al. | 604/22 |
| 4,535,773 | 8/1985 | Voon | 604/51 |
| 4,576,589 | 3/1986 | Kraus et al. | 604/8 |
| 4,588,398 | 5/1986 | Daugherty et al. | 604/164 |
| 4,601,710 | 7/1986 | Moll | 604/165 |
| 4,654,030 | 3/1987 | Moll et al. | 604/165 |
| 4,676,774 | 6/1987 | Semm et al. | 604/26 |
| 4,874,362 | 10/1989 | Wiest et al. | 604/26 |
| 4,902,280 | 2/1990 | Lander | 604/165 |
| 4,931,042 | 6/1990 | Holmes et al. | 604/164 |
| 4,943,280 | 7/1990 | Lander | 604/169 |
| 4,966,578 | 10/1990 | Baier et al. | 604/26 |
| 5,009,643 | 4/1991 | Reich | 604/164 |
| 5,030,206 | 7/1991 | Lander | 604/164 |
| 5,053,016 | 10/1991 | Lander | 604/169 |
| 5,057,082 | 10/1991 | Burchette, Jr. | 604/164 |
| 5,066,288 | 11/1991 | Deniega et al. | 606/172 |
| 5,073,169 | 12/1991 | Raiken | 604/180 |
| 5,104,382 | 4/1992 | Prinkerhoff et al. | 604/165 |
| 5,104,383 | 4/1992 | Shichman | 604/167 |
| 5,112,321 | 5/1992 | Hiltebrandt | 604/264 |
| 5,114,407 | 5/1992 | Burbank | 604/164 |
| 5,122,122 | 6/1992 | Allgood | 604/174 |
| 5,129,885 | 7/1992 | Green et al. | 604/164 |
| 5,137,509 | 8/1992 | Freitas | 604/26 |
| 5,147,316 | 9/1992 | Castillenti | 606/185 |
| 5,152,754 | 10/1992 | Plyley et al. | 604/164 |
| 5,158,552 | 10/1992 | Borgia et al. | 604/165 |

FOREIGN PATENT DOCUMENTS 0131027  10/1960  U.S.S.R. ............................ 604/164

Primary Examiner—Stephen C. Pellegrino
Assistant Examiner—Glenn K. Dawson
Attorney, Agent, or Firm—I. C. Waddey, Jr.

[57] ABSTRACT

This invention relates to a safety trocar which requires less insertion force to penetrate the abdominal wall than the prior art devices. The trocar has a blade with a shaft and body. The body includes a pointed tip which makes the initial incision in the abdominal wall of the patient. The body of the blade has a shoulder which is of a reduced size as compared to the body thereby creating a stepped relationship between the body and the shoulder of the blade. The thickness of the step formed by the relationship of the diameter of the body and shoulder is substantially the same thickness as the wall thickness of the cylindrical cannula that fits over the blade. The inside diameter of substantially the entire length of the cannula is substantially the same as the outside diameter of the body of the blade. The proximal end of the cannula has a number of slits cut in an axial direction along the cannula, thereby creating finger-like segments at the distal end of the cannula that are formed of a material that is biased radially inwardly. The slits allow the fingers, which are biased radially inwardly, to collapse around the shoulder of the blade and the ends of the fingers have a shape substantially designed to conform to the outer shape of the body of the blade so that the biasing forces of the fingers causes the fingers to grip the shoulder of the blade. The structure creates a smooth transition between the blade through the body region and on to the outer surface of the cannula so that the forces necessary to cause the trocar to penetrate the abdominal wall are substantially reduced.

18 Claims, 3 Drawing Sheets

TROCAR WITH PROFILE TO REDUCE INSERTION FORCE

BACKGROUND OF THE INVENTION

Generally, my invention relates to a trocar which penetrates a body cavity for laprascopic procedures. More specifically, the present invention relates to a trocar with an improved profile which reduces the force necessary for insertion of the trocar into a body cavity. The improved trocar of this invention allows the user of the trocar to perform the insertion procedure with greater safety than through the use of devices known in the prior art.

Trocars are devices used in conjunction with minimal invasive surgery. The trocar is a combination of a blade and a cannula. The device is constructed so that once it penetrates the various body layers and enters a body cavity, the blade can be withdrawn leaving a cannula functioning as a channel for the insertion of surgical instruments into the body cavity for use in performing the surgical procedure.

In its specific application, this invention relates to and is used in connection with a laprascopic procedure such as laprascopic cholecystectomy. Such a procedure usually begins by the surgeon inserting a hollow needle into the abdominal cavity to introduce a gas under pressure to insufflate the cavity for creation of a work space for the procedure. A self sealing trocar, consisting of an outer cannula and an inner penetrating mandrel or blade extended beyond the distal end of the assembly, is then used to penetrate the abdominal wall. The outer cannula is forced, along with the blade, through the various layers forming the outer wall of the body and finally through the peritoneum and into the abdominal cavity. After the penetration process is completed, the blade is withdrawn, creating a channel along the length of the cannula through which various instruments are inserted for performing the laprascopic procedure.

A problem that occurs occasionally during the trocar insertion procedure is the inadvertent puncturing of organs inside the cavity with the trocar blade. If an organ is inadvertently punctured during the procedure, what began as minimal invasive surgery may become a major operation and may require open cavity surgery to repair the punctured organ.

It has been determined that one of the reasons that the procedure occasionally results in a punctured organ is because of the magnitude and inconsistency of the force required to penetrate the abdominal wall. Studies have shown [See, e.g., Corson, et al, *Journal of Reproductive Medicine* pp. 282-84 (1989)] that the insertion force required for both disposable and reusable trocars varies from 3.0 to 34 lbs.

When the trocar is being inserted through the abdominal wall, the physician is applying pressure against the proximal end of the trocar and the dominant counteracting force to the force created by the pressure of the physician is the force exerted by the insufflation gas on the abdominal wall. For typical insufflation pressures of 15 mm of Hg., the total force exerted on the wall is less than 15 lbs. for a typical 50 sq. in. abdominal size. Insertion forces substantially greater than 15 lbs. will compress the abdomen substantially toward vital organs. Often the surgeon meets high resistive forces due to the strong fascia layers which halt smooth entry of the trocar. Final penetration often occurs in a quick catastrophic fashion such that the physician is unable to react to avoid puncturing vital organs.

The fascia layer is a sinewy web-like structure of substantial strength. With trocars of the type that have been used in the past, particularly those in which there is a step created on the outer surface of the trocar by the engagement of the cannula about the outer perimeter blade extending from the distal end of the cannula, the step of such prior structures tends to bind against the fascia layer and cause greater resistance to penetration. When enough pressure is applied to the proximal end of the trocar, it will eventually force the stepped shoulder of the prior art cannula through the fascia and when that occurs, the resisting force against the force being applied by the physician is quickly released so that the trocar proceeds rapidly through the abdominal wall.

The prior art has primarily been directed at attempts to react to the problem rather than to eliminate the problem. The efforts of the prior art include so-called "safety shields" which are designed to cover the blade as soon as the peritoneum has been penetrated. U.S. Pat. Nos. 4,535,773 and 4,601,710 disclose such shields that enclose the blade. These shields are equipped with a spring loaded bias. The act of pushing the distal end of the trocar assembly against the abdominal wall moves the shield against the bias in the proximal direction, thereby exposing the blade. When the friction force between the abdominal wall layers and the safety shield exceed the bias force, the trocar enters the body cavity, the friction forces are released and the spring bias force causes the shield to move distally to again cover the blade. The problem with the prior art is two-fold. First, the blade breaks through the peritoneum significantly prior to the shield and, therefore the blade must be inside the cavity by a substantial length before the shield activates. Second, and compounding the problem, is the fact that the shield diameter is larger than the blade, thereby increasing the frictional forces from surrounding tissue as the trocar is forced through the abdominal wall. Because of the great force that must be exerted against the trocar to cause it to penetrate the abdominal wall, and since that force is increased by the increased diameter of the shield surrounding the blade, once actual penetration into the abdominal cavity is achieved, the resisting force is released and the tendency is for the trocar to accelerate rapidly into the body cavity and puncture vital organs.

In the use of prior art devices, including those devices carrying safety shields, the insertion forces necessary to cause penetration are often substantially greater than the 15 lbs. of force created by the insufflation process. Thus, the abdomen is compressed substantially toward vital organs so that the shield may not have time or room to activate. The bias force on the socalled "safety shield" must be overcome before the blade is exposed and thus adds to the overall insertion force requirement. Also, the force required to penetrate the cavity increases the pressure of the insufflating gas inside the cavity by decreasing the volume of the cavity and thereby increasing the risk of embolism.

What is needed then is a safety trocar which will substantially reduce the force required for insertion of the trocar.

It is therefore an object to the present invention to provide a safety trocar which does in fact reduce the insertion force requirement.

It is a further object of the present invention to provide a safety trocar that reduces the insertion force requirements yet is simple and easy to manufacture at a minimum cost as compared to prior art devices.

It is still another object of the present invention to provide a safety trocar which has a unique profile that reduces the insertion force requirements when the trocar is used to penetrate the abdominal wall.

It is still another object of the present invention to provide a safety trocar that requires a consistent and low insertion force, preferably in the 2 to 4 lb. range.

These and other objects of the invention will be more clearly understood when the detailed description of the preferred embodiment is considered in conjunction with the drawings made a part of this application.

SUMMARY OF THE INVENTION

This invention relates to a safety trocar which requires less insertion force to penetrate the abdominal wall than the prior art devices. The trocar has a blade with a shaft and body. The body includes a pointed tip which makes the initial incision in the abdominal wall of the patient. The body of the blade has a shoulder which is of a reduced size as compared to the body thereby creating a stepped relationship between the body and the shoulder of the blade. The thickness of the step formed by the relationship of the diameter of the body and shoulder is substantially the same thickness as the wall thickness of the cylindrical cannula that fits over the blade. The inside diameter of substantially the entire length of the cannula is substantially the same as the outside diameter of the body of the blade. However, the distal end of the cannula has a number of slits cut in an axial direction along the cannula, thereby creating finger-like segments at the distal end of the cannula that are formed of a material that is biased radially inwardly. The slits allow the fingers to collapse around the shoulder of the blade and the ends of the fingers have a shape substantially designed to conform to the outer shape of the body of the blade so that the biasing forces of the fingers causes the fingers to grip the shoulder of the blade. The structure creates a smooth transition between the blade through the body region and on to the outer surface of the cannula so that the forces necessary to cause the trocar to penetrate the abdominal wall are substantially reduced. The smooth, uninterrupted profile of the trocar along its outer surface allows the trocar to penetrate the abdominal wall without encountering additional resistance. Stated conversely, there are no discontinuities in the cross-sectional profile of the trocar moving in an axial direction.

Once the trocar has entered the abdominal cavity, retracting the blade into the cannula is easily accomplished because the fingers will spread open in response to axial force on the blade in the proximal direction while holding the cannula in place. This force causes the fingers to ride up over the surface connecting the shoulder to the body of the blade and allows the blade to be withdrawn into the cannula and thereafter removed from the cannula so that surgical instruments can be inserted through the cannula into the body cavity.

DESCRIPTION OF THE PREFERRED EMBODIMENT

Figure 1:
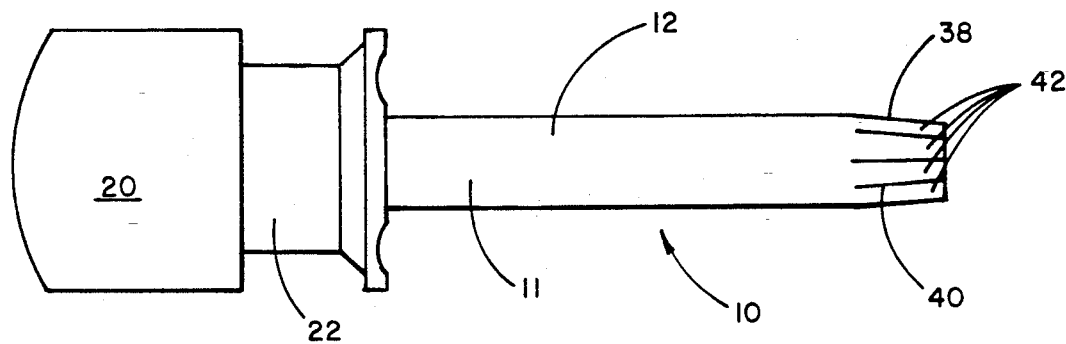
FIG. 1 shows a plan view of the trocar with the blade in the retracted position.

Referring now to the drawings wherein like numerals represent like parts throughout, in FIG. 1, the trocar of the present invention is illustrated in a plan view. The trocar includes a cannula 12 and a blade 14 (FIG. 3) telescopically positioned within the cannula 12. The cannula 12 is cylindrically shaped having an axis 11 and a wall thickness t (see FIG. 4). In practical application, the cross-section of the cannula is circular having an inside diameter i/d (see FIG. 2). Of course the cross-sectional shape of the cannula could be varied to be oval, elliptical, octagonal or other shapes although such shapes would be awkward and less practical than the circular shape which is the preferred embodiment of the invention.

The trocar has a distal end 16 and a proximal end 18. At the proximal end of the trocar there is a grip 20 which is formed either integrally with or connected to the proximal end of the shaft 26 of the blade 14. At the proximal end of the trocar, the cannula has a base 22 which is either formed integrally with the cannula or is attached thereto. The cylindrical shape of the cannula provides a channel 23 through which the blade 14 connected to blade shaft 26 coaxially pass. The grip 20 has a sleeve 24 which creates a chamber 25 into which the base 22 can be seated. The shape of the outside of base 22 generally conforms to the shape of the sleeve 24 so that the distal end of the cannula and blade mate in telescoping fashion. A rim 27 extends radially outwardly from the base 22 to act as a stop so that when the blade is pushed in the direction of the proximal end while holding the base 22 in a substantially stationary position, the blade will protrude from the proximal end of the cannula in a very precise manner as will be described more specifically in conjunction with the illustration shown in FIG. 4 of the drawings. Alternatively, the proximal end of the base 22 can seat against the proximal end of the chamber 25 to create the appropriate relationship between the blade and the cannula when the blade is extended from the cannula at the proximal end of the trocar.

Figure 2:
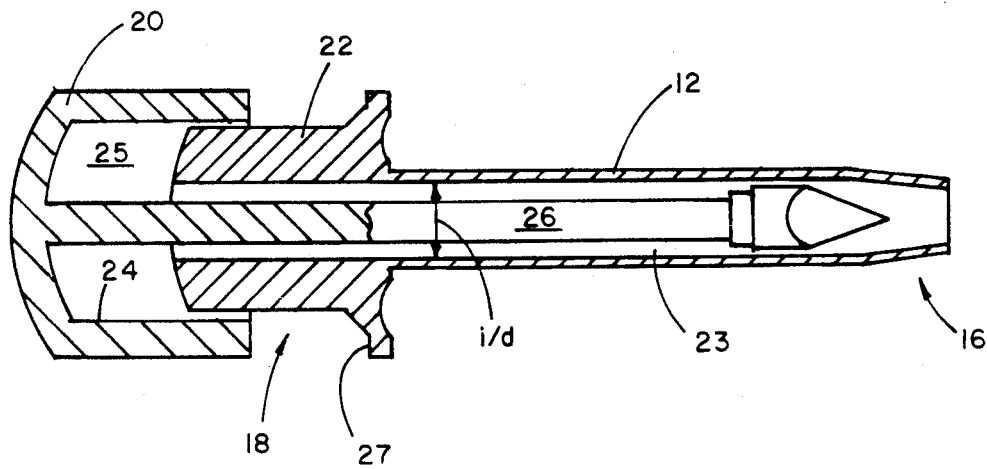
FIG. 2 shows a cross-sectional view of the assembled trocar with the blade in the retracted position.

As can be seen from FIG. 2, the blade can be removed completely from the cannula by moving the blade in the proximal direction relative to the cannula. On the other hand, the blade cannot be extended beyond the position shown in FIG. 4 because either the rim 27 and/or the distal end of the base 22 bind against the grip 20.

Figure 3:
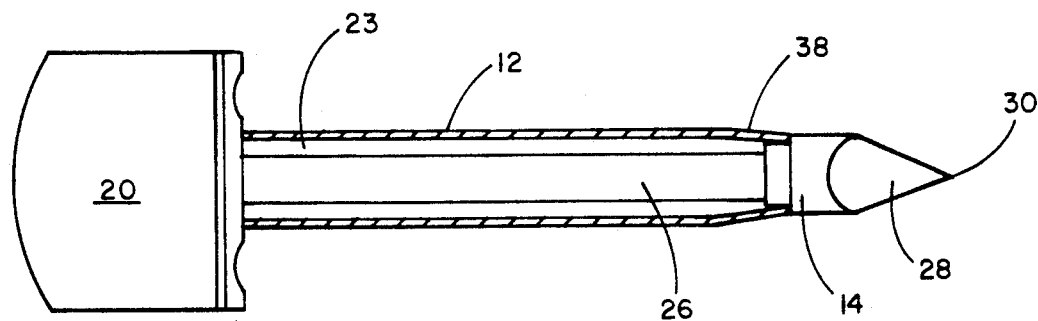
FIG. 3 shows the trocar with the blade extended and the cannula in cross-section.
Figure 4:
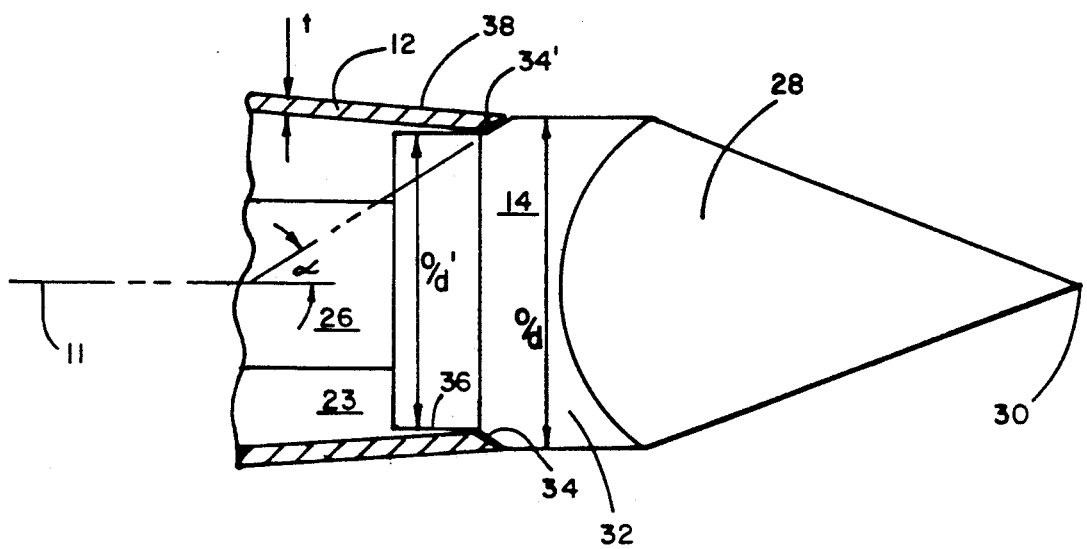
FIG. 4 shows a magnified view of the distal end of the trocar with the cannula shown in cross-section.
Figure 5:
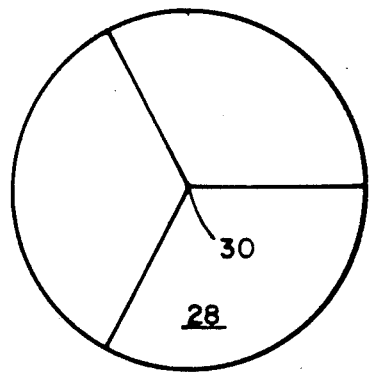
FIG. 5 shows an end view of the blade.

Looking now at FIGS. 3 and 4, the blade has a tip 28 and a point 30. Tip 28 and point 30 are formed at the distal end of the body 32 of the blade 14, the body 32 having an outside diameter o/d substantially equal to but slightly less than the inside diameter i/d of the cannula 11. Thus, when the blade is retracted into the cannula, the body 32 of the blade 14 is of a size and shape that will allow it to pass through the channel 23 of the cannula and to be removed from the trocar at the proximal end of the device.

The body 32 of the blade has a step-down shoulder 36 which has an outside diameter o/d' which is preferably 2t smaller than the outside diameter o/d of the body 32. Again, the description of the body 32 and the shoulder 36 contemplates the cross-section of those elements to be circular which is the preferred embodiment of the invention, but as indicated earlier, those cross-sections could be oval, elliptical, oblong, hexagonal or the like. However, it is generally anticipated that the cross-sectional shape of the shoulder 36 and the body 32 is the same as the cross-sectional shape of cannula 12.

Referring again to FIG. 1, the distal end of the cannula 12 has multiple slits 40 which form fingers 42 extended axially along the length of the distal end of the cannula. The section of the cannula having the fingers 42 is constructed from memory material. The memory forces of the memory material are directed radially inwardly in relationship to the longitudinal axis of the trocar and thus the section of the distal end of the cannula including the fingers 42 is forced to a minimum outside diameter which is smaller than or equal to the outside diameter of the body 32 of the blade 14. The fingers 42 being biased radially inwardly cause the distal end of the cannula 12 to have a conical or tapered 38 shape except when the body 32 of the blade 14 is being retracted into the cannula 12. In the preferred embodiment, the fingers 42 are approximately one inch long so that the increase in the diameter of the outside of the trocar from the body 32 to the cannula as the trocar passes through the abdominal wall will be 2t over a length of one inch.

As can be seen from FIG. 4, the shoulder 36 is connected to the body 32 by an annular ramp 34. The tips of the fingers 42 have ramp engaging surfaces 34' which are of a shape that mate with the annular ramp 34. In the preferred imbodiment of the invention, the angle α of the annular ramp to the axis of the cannula in any plane that includes the axis of the cannula and passes through the annular ramp is in a range of between 5° to 60°.

Because of the relationship between the base and the grip at the proximal end of the trocar, the relative lengths of the cannula 12 and the blade shaft 16 are controlled such that the blade 14, when extended relative to the cannula in the direction of the distal end of the trocar can only go a distance that will allow a mating relationship between the annular ramp 34 and the ramp engaging surfaces 34'. This leaves little or no gap between the body 32 of the blade 14 and the tips of the fingers 42. In addition, as can be seen from FIG. 4, there is a smooth transition in the cross-section of the trocar from the blade to the cannula, thereby eliminating any stepped relationship between the blade and the cannula.

Figure 6:
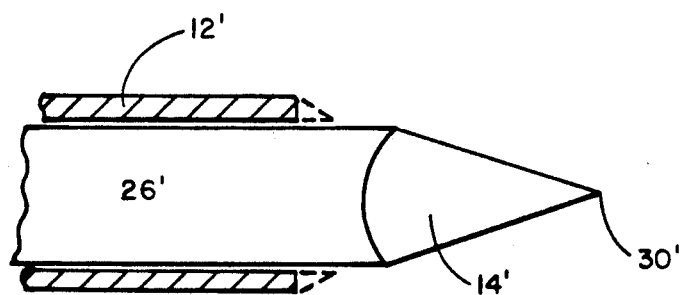
FIG. 6 shows a side view of the tip of the distal end of a prior art device with the cannula and cross-section.

The present invention has eliminated the discontinuous transition from the blade to the cannula of the type illustrated in FIG. 6, which shows one example of the prior art devices. As can be seen from FIG. 6, the blade 14' which is at the end of the shaft 26' telescopes from the cannula 12' but creates a discontinuous transition from the blade to the cannula, either an abrupt one as is shown in full lines or a slightly modified but still problematic transition as shown in broken lines.

Figure 7:
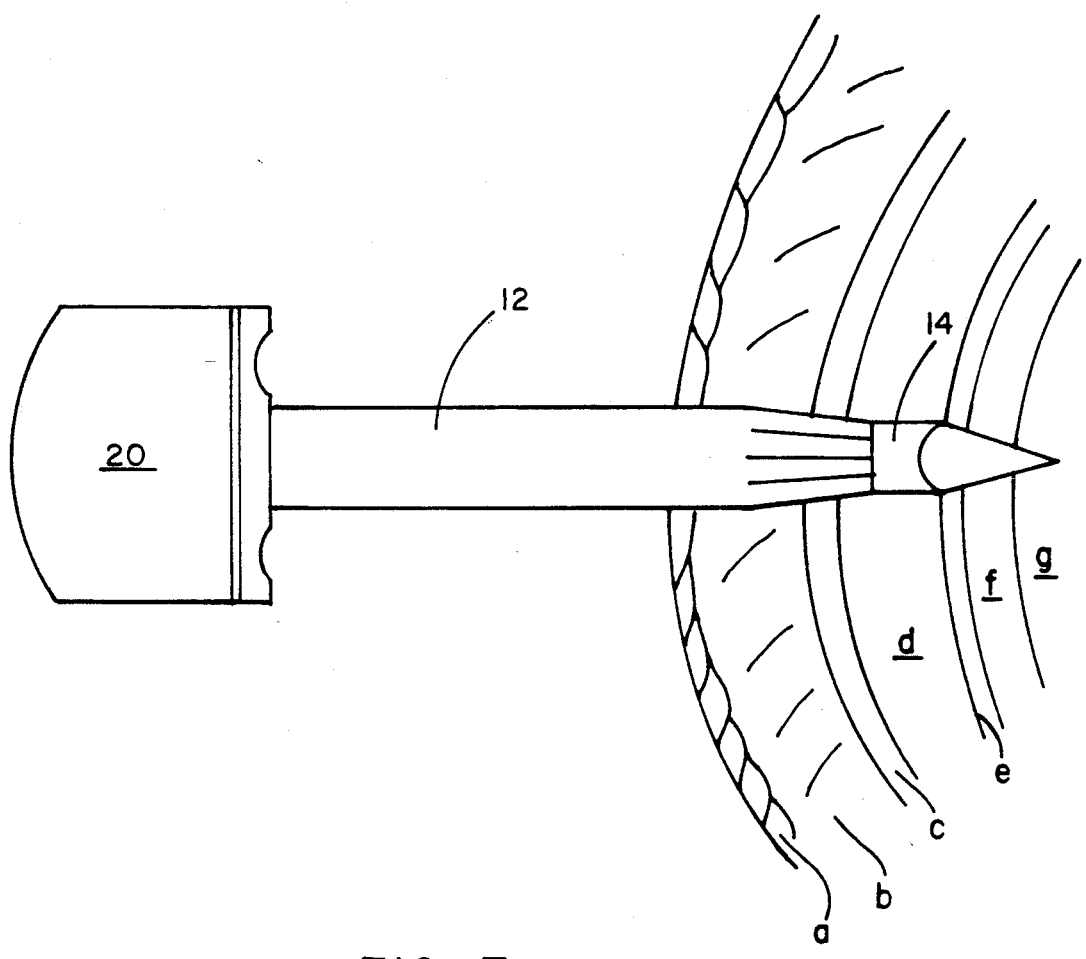
FIG. 7 shows the trocar with the blade extended and being inserted into the abdominal cavity through the abdominal wall.

Referring now to FIG. 7, the operation of the trocar is illustrated as it passes through the abdominal wall. In FIG. 7, the blade 14 protrudes from the distal end 16 of the cannula 12 and passes through the skin layer a, a fat layer b, the fascia c, the muscle d, a second fascia layer e, peritoneum f and into the abdominal cavity g. The cross-section of the trocar is shown to be a smooth transition from the blade to the cannula thus reducing the resistive forces created when the trocar is pressed through the fascia layers which are of considerable strength and difficulty to penetrate.

Once the trocar passes into the abdominal cavity, as can be seen from FIGS. 2, 3 and 4, the grip 20 is then moved relative to the base 22 in the proximal direction. The force applied to the grip 20 in the proximal direction relative to the base 22 causes the annular ramp 34 to apply pressure against the ramp engaging surface 34', one vector of that force being in an outward radial direction thus overcoming the memory forces of the tapered section 38 and causing the fingers 42 to spread and allow the body 32 to retract within the channel 23 within the cannula 12. Once the fingers 42 have passed over the body 32, they will tend, as a result of the memory forces of the material used to manufacture the cannula, move radially inwardly over the tip 28 back to the position as shown in FIGS. 1 and 2. This configuration of the cannula after the blade 14 is removed from the trocar allows the surgical instruments to pass through the cannula in order to perform the surgical procedures contemplated.

Having described a preferred embodiment of my invention, the scope of the invention will be defined by the claims as follows.

What I claim is:

1. A trocar including:
   a. a cannula having a proximal end and a distal end, said distal end of said cannula having an outer perimeter surface;
   b. a blade having a blade tip and a blade body, said blade body having an outer perimeter surface;
   c. means coaxially fitting the blade within the cannula;
   d. means controlling the extent to which the blade can be extended beyond the distal end of the cannula; and
   e. means creating a step-less connection between the blade body and the distal end of the cannula when the blade body is extended beyond the distal end of the cannula, whereby the outer perimeter surface of the blade body corresponds to the outer perimeter surface of the distal end of the cannula.

2. A trocar as claimed in claim 1 wherein the means creating a step-less connection between the blade and the cannula include providing a shoulder on the blade.

3. A trocar as claimed in claim 2 wherein the cannula has fingers on the distal end thereof.

4. A trocar as claimed in claim 3 wherein the fingers retract about the blade to engage the shoulder thereof.

5. A trocar as claimed in claim 4 wherein the fingers are expandable to allow the blade to retract coaxially within the cannula.

6. A trocar as claimed in claim 2 wherein the body is connected to the shoulder by an annular ramp.

7. A trocar as claimed in claim 6 wherein the annular ramp is at an angle of between 5° to 60° to the axis of the cannula in any plane that includes the axis of the cannula and passes through the annular ramp.

8. The trocar as claimed in claim 7 wherein the cannula has fingers at the distal end thereof, and said fingers have ramp engaging surfaces that mate with the annular ramp.

9. The trocar as claimed in claim 8 wherein the ramp engaging surfaces are substantially complementary to the shape of at least a portion of the annular ramp.

10. A trocar as claimed in claim 1 wherein the means controlling the extent to which the blade can be extended beyond the distal end of the cannula include a base on the proximal end of the cannula and a grip connected to the blade.

11. A trocar as claimed in claim 10 including a shaft between the grip and the blade.

12. A trocar as claimed in claim 11 wherein the base of the cannula fits within the grip.

13. A trocar as claimed in claim 12 wherein the grip includes a channel with the base fitting within said channel.

14. A trocar as claimed in claim 10 wherein the base includes a flange.

15. A trocar as claimed in claim 14 wherein the flange abuts the grip.

16. A trocar including
  a cylindrically shaped cannula having a base at one end thereof and axially directed slots at the other end thereof;
  b. said axially directed slots forming fingers, each finger having a base at one end and a tip at an opposite end;
  c. the other end of said cannula being formed of a material that is biased radially inwardly so that the fingers will tend to contract and cause the other end of the cannula to have a conical shape;
  d. the slots in the other end of the cannula are of a dimension that will allow the fingers to contract at the most a distance that will cause the outside diameter of the cannula at the tips of the fingers to be approximately 2t less than the outside diameter of the cannula at the base of the fingers where t is the thickness of the wall of the cannula;
  e. a blade coaxially fitted within the cannula; and
  f. said blade including a body and a shoulder, the body having an outside diameter substantially equal to the inside diameter of the cannula and the shoulder having an outside diameter 2t less than the inside diameter of the cannula.

17. The trocar as claimed in claim 16 including means controlling the extent that the blade can be extended beyond the other end of the cannula.

18. The trocar as claimed in claim 16 wherein the bias of the material causes the fingers to contract about the shoulder of the blade to create a stepless transition between the blade body and the other end of the cannula when the blade is extended its maximum distance beyond the other end of the cannula.

* * * * *